United States Patent
Lightstone et al.

(10) Patent No.: US 8,962,511 B2
(45) Date of Patent: Feb. 24, 2015

(54) SYNTHETIC CATALYSTS THAT SEPARATE $CO_2$ FROM THE ATMOSPHERE AND GAS MIXTURES

(75) Inventors: Felice C. Lightstone, Fremont, CA (US); Sergio E. Wong, Campbell, CA (US); Edmond Y. Lau, Dublin, CA (US); Joe H. Satcher, Jr., Patterson, CA (US); Roger D. Aines, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 815 days.

(21) Appl. No.: 12/967,262

(22) Filed: Dec. 14, 2010

(65) Prior Publication Data
US 2011/0151537 A1 Jun. 23, 2011

Related U.S. Application Data

(60) Provisional application No. 61/287,375, filed on Dec. 17, 2009.

(51) Int. Cl.
| | |
|---|---|
| B01J 21/18 | (2006.01) |
| C12P 7/04 | (2006.01) |
| B01D 53/14 | (2006.01) |
| B01D 53/62 | (2006.01) |
| C12N 9/02 | (2006.01) |
| B01D 53/86 | (2006.01) |

(52) U.S. Cl.
CPC ............... *C12P 7/04* (2013.01); *B01D 53/1475* (2013.01); *B01D 53/1493* (2013.01); *B01D 53/62* (2013.01); *C12N 9/0073* (2013.01); *B01D 53/86* (2013.01); *B01D 2252/60* (2013.01); *B01D 2255/20746* (2013.01); *B01D 2255/20761* (2013.01); *B01D 2255/20792* (2013.01); *B01D 2257/504* (2013.01); *B01D 2258/0283* (2013.01); *B01D 2258/06* (2013.01); *Y02C 10/04* (2013.01); *Y02C 10/06* (2013.01)
USPC ......................................................... 502/174

(58) Field of Classification Search
USPC ......................................................... 502/300
See application file for complete search history.

(56) References Cited

U.S. PATENT DOCUMENTS

| | | | |
|---|---|---|---|
| 7,828,883 B2 | 11/2010 | Aines et al. | |
| 2007/0170060 A1 | 7/2007 | Bourcier et al. | |
| 2010/0303694 A1 | 12/2010 | Aines | |
| 2011/0091955 A1 * | 4/2011 | Constantz et al. | ............ 435/168 |

FOREIGN PATENT DOCUMENTS

WO    WO 0142259 A1 *  6/2001

* cited by examiner

*Primary Examiner* — Melvin C Mayes
*Assistant Examiner* — Kenneth Vaden
(74) *Attorney, Agent, or Firm* — Eddie E. Scott

(57) ABSTRACT

The creation of a catalyst that can be used for a wide variety of applications including the steps of developing preliminary information regarding the catalyst, using the preliminary information to produce a template of the catalyst, and using the template of the catalyst to produce the catalyst.

3 Claims, 1 Drawing Sheet

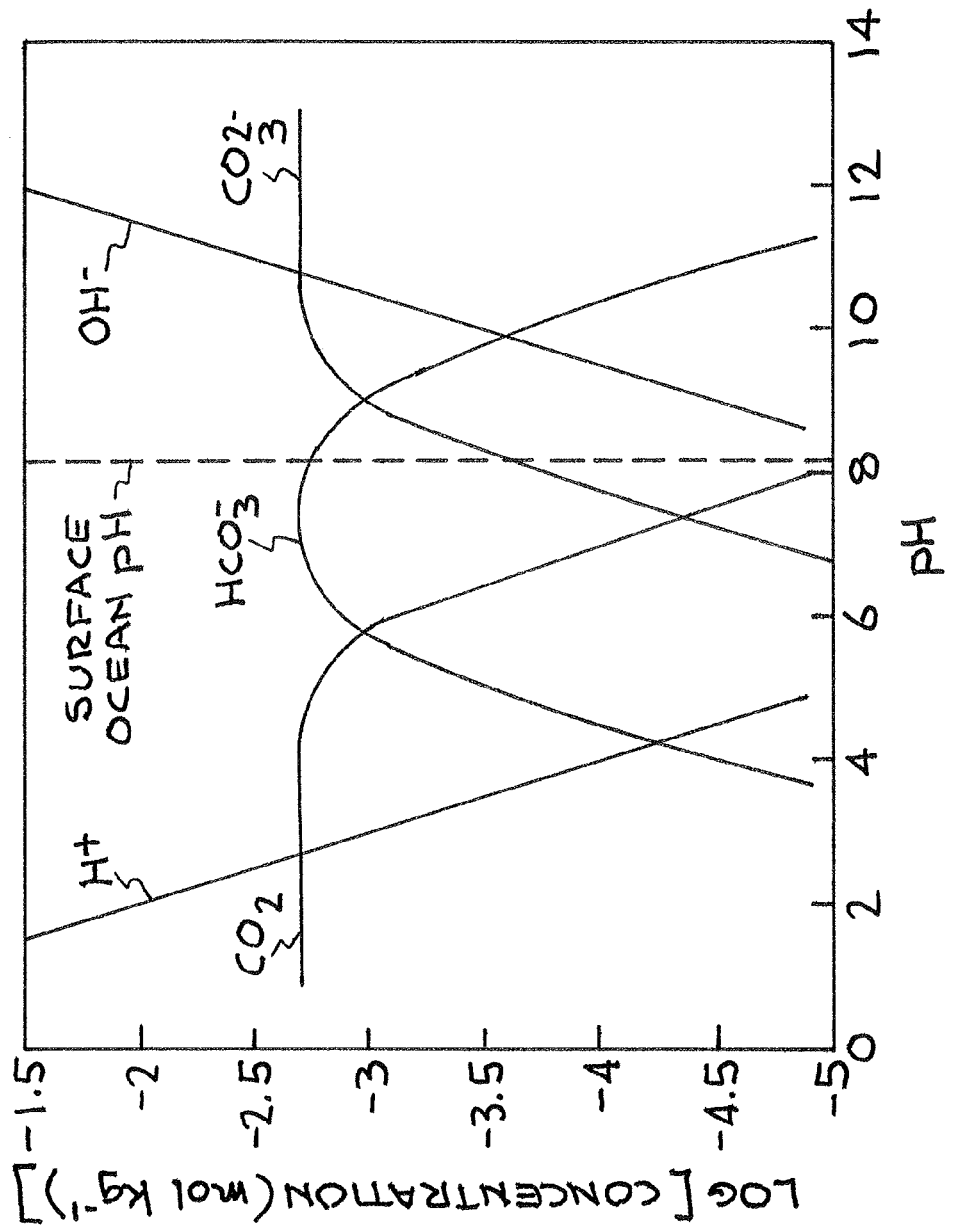

US 8,962,511 B2

SYNTHETIC CATALYSTS THAT SEPARATE $CO_2$ FROM THE ATMOSPHERE AND GAS MIXTURES

CROSS-REFERENCE TO RELATED APPLICATIONS

The present application claims benefit under 35 U.S.C. §119(e) of U.S. Provisional Patent Application No. 61/287,375 filed Dec. 17, 2009 entitled "Synthetic Catalysts that Separate $CO_2$ from the Atmosphere and Gas Mixtures," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to carbon dioxide and more particularly to removal of carbon dioxide from the atmosphere and gas mixtures 2. State of Technology Direct separation of $CO_2$ from the atmosphere is an emerging technology option. Living creatures have already conquered this technologically difficult reaction by catalyzing the reaction of CO2 to $CO_3H$— with carbonic anhydrase. In recent years a growing awareness of $CO_2$ atmospheric levels sparked interest in developing rapid ways to absorb carbon dioxide from industrial gas streams. Most industrial separation processes for $CO_2$ involve a liquid in which the dissolved $CO_2$ ionizes, greatly increasing its solubility and absorption rate. The slow step in such processes is well known to be the formation of carbonic acid. This reaction controls the uptake of carbon dioxide by the ocean because it is just slow enough to cause a significant mass transfer limitation at the water's surface. This mass transfer limitation also applies to industrial gas separations and results in overall decreases in rate of factors in excess of 1000× over that which could be obtained if the hydration of the $CO_2$ were not the rate limiting step. Speeding such processes through the use of catalysts or enzymes would permit smaller and less expensive separation processes to remove $CO_2$ from industrial gas emissions, and be fast enough to permit removal of $CO_2$ from the atmosphere.

In recent years a growing awareness of $CO_2$ atmospheric revels sparked interest in. developing rapid ways to absorb carbon dioxide from industrial gas streams. Most industrial separation processes for $CO_2$ involve a liquid in which the dissolved $CO_2$ ionizes, greatly increasing its solubility and absorption rate. The slow step in such processes is well known to be the formation of carbonic acid. This reaction controls the uptake of carbon dioxide by the ocean because it is just slow enough to cause a significant mass transfer limitation at the water's surface. This mass transfer limitation also applies to industrial gas separations and results in overall decreases in rate of actors in excess of 1000× over that which could be obtained if the hydration of the $CO_2$ were not the rate limiting step. Speeding such processes through the use of catalysis or enzymes would permit smaller and less expensive separation processes to remove $CO_2$ from industrial gas emissions, and could even conceivably be fast enough to permit removal of $CO_2$ from the atmosphere.

Carbonic anhydrase (CA) efficiently catalysis the reversible hydration of $CO_2$ to carbonic acid. In erythrocytes, its rate kinetics surpasses the $CO_2$ diffusion rate out of the cell. It is a ubiquitous enzyme expressed in prokaryote, and eukaryote organisms. The HMM library and genome assignment server lists 33 CA homologs in the human genome. CAII is the most efficient of the three forms of CA. Deficiency of CAII is associated with renal tubular acidosis and brain calcification, while it also plays a role in bone readsorption. Since its discovery, it sparked great interest due to its highly efficient kinetics and its $Zn^{2+}$ metal center.

Current research into the use of carbonic anhydrase for industrial $CO_2$ capture has received limited publication partially due to the difficulty of maintaining viable enzyme in industrial processes. Trachtenberg et al uses a membrane-countercurrent system originally designed for spacecraft use. Bhattacharya et al uses a spray system with carbonic anhydrase in the spray. Azari and Nemat-Gorgani examined means of using the reversible unfolding of the enzyme, caused by heat, to attach it to more sturdy substrates for industrial use. Yan et al. incorporate single carbonic anydrase molecules in a spherical nanogel and report that greatly improved temperature stability with only moderate loss of activity. Applicants are investigating whether small catalytic mimelics of CA may be more attractive as components of industrial gas separation processes, Creating such mimetics requires knowledge of the catalytic mechanism and possible degradation mechanisms of the catalytic enter.

Experimental and theoretical research contributed to the current understanding of CA's reaction mechanism. Crystallographic studies showed the $Zrt^2$ ion in the CAII binding site is chelated by three hislidine side-chains and a water molecule to yield a tetrahedral coordination geometry. The reaction is thought to occur in three steps: 1) deprotonation of the water ligand to form an activated hydroxyl group, 2) a nucleophilic attack from the hydroxyl oxygen to the carbon atom in $CO_2$ to form an intermediate species, and 3) the displacement of bicarbonate by water, which re-starts the cycle.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention is the creation of a catalyst that can be used for a wide variety of applications. In one embodiment the present invention provides a method of producing a catalyst for harvesting carbon dioxide from a gas mixture. The method includes the steps of developing preliminary information regarding the catalyst for harvesting carbon dioxide from a gas mixture, using the preliminary information to produce a template of the catalyst for harvesting carbon dioxide from a gas mixture, and using the template of the catalyst for harvesting carbon dioxide from a gas mixture to produce the catalyst for harvesting carbon dioxide from a gas mixture.

One embodiment the present invention is the creation of a catalyst that can sequester $CO_2$ from the air and convert the carbon into a water soluble form. It has been shown that $Zn^{2+}$ will work for the catalyst. Various metals have been shown to work in carbonic anhydrase, but different metals have not been shown to work in the small molecule catalysts. Applicants use other metals such as cobalt, copper and iron. Applicants have also designed a method to attach the catalyst to a surface. Applicants' compounds are tethered to a surface to maximize the regeneration of the catalyst.

Another embodiment the present invention is the creation of a catalyst for conversion of methane to methanol. Yet another embodiment the present invention is the creation of a catalyst for water oxidizing using an oxygen evolving catalyst. Another embodiment the present invention is the creation of a catalyst for nitrogen fixation.

Use of the present invention includes capturing $CO_2$ emissions from industrial processes or vehicles or from the air. This included enhanced technology for removing carbon dioxide from industrial gas waste streams, natural gas, and the atmosphere. Other uses of the present invention include conversion of methane to methanol, water oxidizing, and nitrogen fixation The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIG. 1 illustrates the speciation of carbon dioxide in water as a function of pH, and at a constant overall concentration of carbon.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Current carbon dioxide separation schemes for managing $CO_2$ concentrations near atmospheric concentrations utilize water as the separation media. This is because water provides an extremely large factor to separate carbon dioxide from non-ionizable nitrogen and oxygen. These gases are limited to solubilities of around 40 ppm in water—but with appropriate chemical control the ionized species bicarbonate $HCO_3^-$ and carbonate $CO_3$ can have concentrations thousands of times higher. In other words, once the $CO_2$ dissolves in water, it is now a very different molecule than oxygen and nitrogen, with concordant high separation efficiency.

The best hope for speeding up the dissolution is by quickly reacting the $CO_2$ to one of its other, more soluble forms ($HCO_3^-$ or $CO_3^{2-}$) and avoiding the limitation imposed by the low Henry's law coefficient. Any kinetic limitation based on liquid processes starts at the concentration at the air-water interface—this concentration is set by Henry's law. When the concentration on the air side doubles, the water side concentration doubles, as does in general the mass flux of any process in the water transferring $CO_2$ away from the interface. This inherently makes it difficult to design air capture processes. For instance, using identical capture processes for air and coal flue gas, the flue gas process will have a mass flux more than 300 times larger simply due to the increased concentration. This has an enormous influence on process design, since prima facie it suggests that in order to handle a similar amount of $CO_2$, the air capture process would have to be 300 times larger.

The speciation of carbon dioxide in water is therefore critical to both concentration, and to the rate at which water can absorb the gas. FIG. 1 highlights two distinct concentration regions:

Region 1. Below pH 5: dissolved carbon dioxide is low because the unionized species predominate. Total dissolved $CO_2$ can only be increased by increasing the gas pressure of $CO_2$ above the water. This is the carbonated beverage regime—the gas comes out when the pressure is released.

Region 2. Above pH 5: the concentration, and potentially the transfer rate, can be increased by adding a pH buffer to the solution that binds to the protons released which are released in the conversions

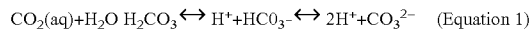

$$CO_2(aq) + H_2O \; H_2CO_3 \leftrightarrow H^+ + HCO_3^- \leftrightarrow 2H^+ + CO_3^{2-} \quad \text{(Equation 1)}$$

In region (2) above pH 5, the ability of water to carry carbon is only limited by the solubility of appropriate buffer species such as substituted amines and strong hydroxides like NaOH.

However, the fact that a solution is capable of carrying a given amount of carbon dioxide does not mean the uptake occurs instantly. The initial dissolution step at below pH 8 involves the gas dissolving in water and undergoing a hydrolysis reaction with water.

$$CO_2(aq) + H_2O \leftrightarrow H_2CO_3 \quad \text{(Equation 2)}$$

where k forward –0.0025 to 0.04 s –t k reverse –10 to 20 s –1

This humble reaction controls the uptake of carbon dioxide by the ocean because it is just slow enough to cause a significant mass transfer limitation at the water's. Once the carbonic acid ($H_2CO_3$) has formed it rapidly equilibrates to the species shown in FIG. 1. The reverse reaction is the chemistry that controls a human's exhaling carbon dioxide (dissolved in the blood). Fortunately there is an enzyme, carbonic anhydrase, that dramatically increases the speed of the reaction (in both directions), permitting the dissolved carbonate to exit our lungs as carbon dioxide. It is an extremely rapid converter of $CO_2$ to $H_2CO_3$, with rates of up to 106 s-' in the form found in human lungs. This is a speed up of 25 million above the uncatalyzed reaction. Mass transfer limitations would appear to restrict the overall speed up to perhaps a factor of 1000 before the air transfer becomes limiting.

A second, and much faster reaction is also prominent when a lot of hydroxide is present:

$$CO_2(aq) + OH^- \leftrightarrow HCO_3^- \quad \text{(Equation 3)}$$

Where k forward –8.5×103 M'''s''r k reverse –2×10$^{-4}$ s'a.

As is typical of this type of nucleophilic reaction, it is very fast, and the rate is a direct function of the hydroxyl concentration. FIG. 1 shows that this concentration becomes overwhelming above pH 10 where the amount of hydroxyl available then dominates the kinetic behavior. However even with a dramatically faster conversion of $CO_2$ to ionized species, the mass transfer limitation is not easily overcome (more than another factor of 10 in reaction speed would be required at 25° C. for the overall rate to be substantially affected by hydroxyl concentration at pH=10. Thus very basic solutions are required for the chemistry to enhance the overall absorption rate. The reverse reaction is not dependant on hydroxyl concentration however, and is relatively slow. This permits us to further refine the previously defined regions:

Region 2A. pH 5-10: uptake of carbon dioxide is slow due to mass transfer limitations. Carbonic anhydrase is critical for natural systems to function in this pH range.

Region 2B. Above pH 10: direct attack of OH' on dissolved carbon dioxide gas results in rapid uptake.

The small molecule catalysts Applicants have identified carbon sequestering catalysts 3 and 4 nitrogen macrocycles with different functional groups attached. Applicants have focused on 4 metals, zinc, cobalt, copper and iron, for the metal centers. Also, the benzimidizole compound provides protection to the metal from becoming polluted. Formulas for three and four nitrogen macrocycles with different functional groups and metals are below.

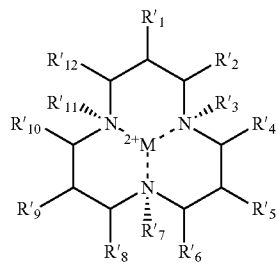

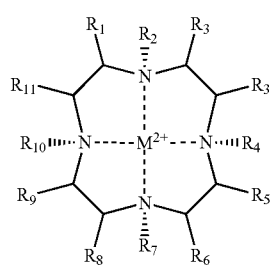

where R=H, $SO_3^{-2}$, PEG, $(CH_2)nCH_3$, OH, $(CH_2)nOH$ and M=an, Co, Cu, Fe.

Formulas for Benzoimi€dizole macrocycle shown with different functional groups and different metal centers are below.

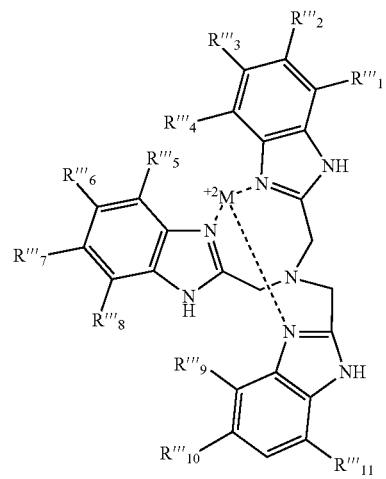

where R H, $SO_3^{-2}$, PEG, $(CH_2)nCH_3$, OH and M=Zn, Co, Cu, Fe.

Carbon dioxide ($CO_2$) sequestration is an application of high interest due to the pressing need to capture large-scale, megaton quantities of $CO_2$ from industrial processes or the atmosphere. For this reason, catalysts that may facilitate this process can have a great environmental impact. In nature, the zinc metalloenzyme carbonic anhydrase II (CAII) hydrates $CO_2$ to carbonic acid extremely efficiently at ambient conditions. Several small molecule mimics of CAII have been designed over the years in order to study the reaction mechanism and attempt to capture this reactivity. Quantum mechanical calculations of two of the most efficient mimetics, 1,4,7,10-tetraazacyclododedacane and 1,5,9-triazacyclododedacane (both complexed with a $Zn^{2+}$ or $Co^{2+}$ ion), were performed to predict the reaction coordinate for $CO_2$ hydration. These calculations showed that the ability of the metal ion to maintain a tetrahedral geometry and to have bicarbonate bind in a unidentate manner were key aspects for the hydration reaction. The catalytic activity of the zinc complexes was insensitive to coordination but coordination higher than four caused product release to be unfavorable for the cobalt complex.

In recent years a growing awareness of $CO_2$ atmospheric levels sparked interest in developing rapid ways to absorb carbon dioxide from industrial gas streams. Most industrial separation processes for $CO_2$ involve a liquid in which the dissolved $CO_2$ ionizes, greatly increasing its solubility and absorption rate. The rate limiting step in such processes is well known to be the formation of carbonic acid. The slow kinetics of this reaction also hinders the uptake of carbon dioxide by the ocean and causes a significant mass transfer limitation at the water's surface. This mass transfer limitation also applies to industrial gas separations and results in overall decreases in rate factors in excess of 1000-fold over that which could be obtained if the hydration of the $CO_2$ were not the rate-limiting step. Accelerating such processes through the use of catalysts or enzymes would permit smaller and less expensive separation processes to remove $CO_2$ from industrial gas emissions and removal of $CO_2$ from the atmosphere.

In biological systems, the reversible hydration of $CO_2$ to bicarbonate occurs at a greater efficiency via catalysis by the zinc metalloenzyme, carbonic anhydrase (CA). In humans, carbonic anhydrase II (CAII) is the most efficient isoform with diffusion limited kinetics. The reaction is catalyzed by zinc-hydroxide which is formed when a water molecule coordinates to the zinc, thereby lowering the water's $pK_a$ to ~7. The reaction mechanism, which follows ping-pong kinetics, occurs as two independent steps. In step one, the zinc-hydroxide in the active site of CA attacks $CO_2$ to form bicarbonate which is subsequently displaced by a water molecule.

In the second step, the zinc bound water loses a proton to a catalytic histidine (His64 in human CAII) and finally into bulk solvent (and buffer) to regenerate the zinc-hydroxide catalyst.

Deprotonation of the water is the rate-limiting step in carbonic anhydrase. The extremely high hydration turnover of $CO_2$ by CAII is ~$10^6$ $sec^{-1}$ at pH 9 and 25° C. The reverse reaction, dehydration of bicarbonate occurs when the solution pH is below 7.

The X-ray crystal structures of many different CAs have been solved and studied in great detail. Crystallographic studies of human CAII show that the enzyme is a monomeric protein consisting of 260 residues. The binding site is shaped like a funnel, with the metal center at the bottom. The coordination geometry of the catalytic zinc is tetrahedral with three histidines (His94, His96, and His119) and a water/hydroxide molecule chelating the metal. The active site can be divided into a hydrophobic half necessary for $CO_2$ binding and a hydrophilic half involved in a hydrogen bonding network of residues and water molecules for efficient proton release. Other divalent metals ($Cu^{2+}$, $Hg^{2+}$, $Fe^{2+}$, $Cd^{2+}$, $Ni^{2+}$, $Co^{2+}$ and $Mn^{2+}$) can bind to CAII, but only $Co^{2+}$ has near wild-type activity ($k_{cat}/K_m$=$8.7 \times 10^7 M^{-1}s^{-1}$ for $Zn^{2+}$ vs $8.8 \times 10^7 M^{-1}s^{-1}$ for $Co^{2+}$). Since $Zn^{2+}$ is a poor spectroscopic species, $Co^{2+}$ has played an important role in studying CA because not only does it utilize a metal-hydroxide catalysis and have near wild-type activity but is also spectroscopically active.

Despite the merits of CAII, current research into the use of carbonic anhydrase for industrial $CO_2$ capture has received limited publication partially due to the difficulty of maintaining viable enzyme in industrial processes. Trachtenberg et al use a membrane-countercurrent system originally designed for spacecraft use. Bhattacharya et al uses a spray system with carbonic anhydrase in the spray. Azari and Nemat-Gorgani examined means of using the reversible unfolding of the enzyme, caused by heat, to attach it to more sturdy substrates for industrial use. Yan et al incorporated single carbonic anhydrase molecules in a spherical nanogel and report greatly improved temperature stability with only moderate loss of activity. A more viable possibility is to use small molecules that mimic the CAII catalytic activity. Creating such mimetics requires incorporating key structural features from the enzyme scaffold and avoiding possible degradation mechanisms of the catalytic center. Fortunately, CA mimetics were developed to study the enzyme's reaction mechanism, and several examples of small molecule CA mimetics exist. They include, to varying degrees, structural features of the enzyme. The most prominent feature is a set of nitrogen electron donors that play the role of the enzyme histidine sidechains. These nitrogen atoms may be part of an imidazole group or as secondary amines, such as in 1,4,7,10-tetraazacyclododecane or 1,5,9-triazacyclododecane, which chelate a metal ion. These two macrocycles when chelated with $Zn^{2+}$ are able to catalyze both the hydration of $CO_2$ and the dehydration of bicarbonate depending on the solution pH exactly as CAII although with a more modest catalytic activity.

The hydration reaction of $CO_2$ catalyzed by N3 and N4 chelating $Zn^{2+}$ and $Co^{2+}$ was investigated using quantum mechanical calculations. All calculations were carried out using the program Gaussian03. Geometry optimizations performed at the B3LYP/6-311+G* level of theory. The catalytically active form of cobalt in carbonic anhydrase is experimentally known to be a high spin quartet (S=3/2); thus, calculations on the cobalt-containing mimics were carried out with a fixed quartet multiplicity. Harmonic frequency calculations were performed on all the structures to characterize the stationary points. Transition states were characterized by a single imaginary frequency. The calculated zero-point energies (ZPE) were not scaled. To investigate the effects of solvation on the hydration reaction, single point calculations using the gas-phase geometries were carried out using a conductor-like polarizable continuum model (CPCM) to approximate solvent effects (water, $\epsilon$=78.4). It has been shown that the solvation free energies from single point PCM calculations using gas-phase geometries from density functional calculations are in reasonable agreement with values obtained from full optimizations. All solvation calculations used the simple united atom topological model (UA0) using UFF radii. Natural population analysis was performed on the optimized structures to assess the charge distributions on the complexes.

Example 1

Catalyst Assisted Solvent Systems

Separation of $CO_2$ from a gas mixture can be accomplished using catalyst modified solvent system with a catalyst produced in accordance with the present invention. Most industrial process for separating $CO_2$ from gas mixtures utilize water/buffer as the primary separation media. This is because water provides an extremely large factor to separated carbon dioxide from non-ionizable gases such as nitrogen and oxygen. The water contains additives that serve to buffer the carbonic acid that forms upon $CO_2$ dissolution, and also to speed the $CO_2$ dissolution process. Typically those additives are amines although in some processes hydroxides (such as NaOH) are used. In this example, the buffering compounds are assisted through the use of a catalyst. The dissolved, attached, embedded or fluid surface confined catalyst speeds the uptake of $CO_2$ by the buffered media. This solves a significant challenge in the normal process of carbon dioxide separation by facilitating the use of lower contact areas required for $CO_2$ removal and expanding the selection of the buffering compounds which can lead to lower overall energy costs associated with recovery.

The catalyst can be produced by developing preliminary information regarding the catalyst for harvesting carbon dioxide from a gas mixture, using the preliminary information to produce a template of the catalyst for harvesting carbon dioxide from a gas mixture, and using the template of the catalyst for harvesting carbon dioxide from a gas mixture to produce the catalyst for harvesting carbon dioxide from a gas mixture. The step of developing preliminary information regarding the catalyst for harvesting carbon dioxide from a gas mixture includes developing preliminary information regarding a molecule having potential energy surfaces around a metal center that will optimize reaction with carbon dioxide. The step of using the preliminary information to produce a template of the catalyst for harvesting carbon dioxide from a gas mixture includes generating a selection of linking atoms to compose a scaffold on the metal center that will optimize reaction with carbon dioxide.

The step of developing preliminary information regarding the catalyst for harvesting carbon dioxide from a gas mixture includes using molecule mimics. Applicants have used small molecule mimics of CAII in order to study the reaction mechanism and attempt to capture this reactivity. Quantum mechanical calculations of two of the most efficient mimetics, 1,4,7,10-tetraazacyclododedacane and 1,5,9-triazacyclododedacane (both complexed with a $Zn^{2+}$ or $Co^{2+}$ ion), were performed to predict the reaction coordinate for $CO_2$ hydration. These calculations showed that the ability of the metal ion to maintain a tetrahedral geometry and to have bicarbonate bind in a unidentate manner were key aspects for the hydration reaction. The catalytic activity of the zinc complexes was insensitive to coordination but coordination higher than four caused product release to be unfavorable for the cobalt complex.

Applicants have examined $CO_2$ hydration as catalyzed by 1,4,7,10-tetraazacyclododedacane and 1,5,9-triazacyclododedacane (denoted N4 and N3, respectively) chelating both $Zn^{2+}$ and $Co^{2+}$ to investigate the reaction mechanism of these two metals and determine the cause for the difference in activity seen in human CAII. The hydration reaction of $CO_2$ catalyzed by N3 and N4 chelating $Zn^{2+}$ and $Co^{2+}$ was investigated using quantum mechanical calculations. All calculations were carried out using the program Gaussian03. Geometry optimizations were performed at the B3LYP/6-311+G* level of theory. The catalytically active form of cobalt in carbonic anhydrase is experimentally known to be a high spin quartet (S=3/2); thus, calculations on the cobalt-containing mimics were carried out with a fixed quartet multiplicity. Harmonic frequency calculations were performed on all the structures to characterize the stationary points. Transition states were characterized by a single imaginary frequency. The calculated zero-point energies (ZPE) were not scaled. To investigate the effects of solvation on the hydration reaction, single point calculations using the gas-phase geometries were carried out using a conductor-like polarizable continuum model (CPCM) to approximate solvent effects (water, $\epsilon=78.4$). It has been shown that the solvation free energies from single point PCM calculations using gas-phase geometries from density functional calculations are in reasonable agreement with values obtained from full optimizations. All solvation calculations used the simple united atom topological model $(UA0)^i$ using UFF radii. Natural population analysis was performed on the optimized structures to assess the charge distributions on the complexes.

Example 2

Methane Monooxygenase Catalyst

Conversion of methane to methanol can be accomplished using a methane monooxygenase catalyst produced in accordance with the present invention. Methane monooxygenase, or MMO, is an enzyme capable of oxidizing the C—H bond in methane as well as other alkanes. Methane monooxygenase belongs to the class of oxidoreductase enzymes. There are two well-studied forms of MMO: the soluble form (sMMO) and the particulate form (pMMO). The active site in sMMO contains a di-iron center bridged by an oxygen atom (Fe—O—Fe), whereas the active site in pMMO utilizes copper, although some propose that pMMO also uses iron. Structures of both proteins have been determined by X-ray crystallography; however, the location and mechanism of the active site in pMMO is still poorly understood and is an area of active research.

The methane monooxygenase catalyst is produced by developing preliminary information regarding the methane monooxygenase catalyst for conversion of methane to methanol, using the preliminary information to produce a template of the, and using the template of the catalyst to produce the methane monooxygenase catalyst for conversion of methane to methanol. The step of developing preliminary information regarding the methane monooxygenase catalyst for conversion of methane to methanol includes developing preliminary information regarding a molecule having potential energy surfaces around a metal center that will optimize reactions. The step of using the preliminary information to produce a template of the methane monooxygenase catalyst for conversion of methane to methanol includes generating a selection of linking atoms to compose a scaffold on the metal center that will optimize reactions.

Example 3

Oxygen Evolving Complex Catalyst

Water oxidizing can be accomplished using a oxygen evolving complex catalyst produced in accordance with the present invention. The oxygen evolving complex, (OEC) also known as the water-splitting complex, is a water oxidizing enzyme involved in the photooxidation of water during the light reactions of photosynthesis. Based on a widely accepted theory from 1970 by Kok, the complex can exist in 5 states: $S_0$ to $S_4$. Photons trapped by photosystem II move the system from state $S_0$ to $S_4$. $S_4$ is unstable and reacts with water to produce free oxygen. The OEC appears to have a metalloenzyme core containing both manganese and calcium, with the empirical formula for the inorganic core of $Mn_4Ca_1O_xCl_{1-2}(HCO_3)_y$.

The oxygen evolving complex catalyst can be produced by developing preliminary information regarding the catalyst for water oxidizing, using the preliminary information to produce a template of the catalyst, and using the template of the catalyst to produce the catalyst for water oxidizing. The step of developing preliminary information regarding the catalyst includes developing preliminary information regarding a molecule having potential energy surfaces around a metal center that will optimize reactions. The step of using the preliminary information to produce a template of the catalyst for water oxidizing includes generating a selection of linking atoms to compose a scaffold on the metal center that will optimize reactions.

Example 4

Nitrogen Fixation Catalyst

Nitrogen fixation can be accomplished using a catalyst produced in accordance with the present invention. Nitrogen fixation is the process by which nitrogen ($N_2$) is converted into ammonia. This process is essential for life because fixed nitrogen is required to biosynthesize the basic building blocks of life, e.g. nucleotides for DNA and RNA and amino acids for proteins. Formally, nitrogen fixation also refers to other abiological conversions of nitrogen, such as its conversion to nitrogen dioxide.

The nitrogen fixation catalyst can be produced by developing preliminary information regarding the catalyst, using the preliminary information to produce a template of the catalyst, and using the template of the catalyst to produce the nitrogen fixation catalyst. The step of developing preliminary information regarding the nitrogen fixation catalyst includes developing preliminary information regarding a molecule having potential energy surfaces around a metal center that will optimize reactions. The step of using the preliminary information to produce a template of the nitrogen fixation catalyst includes generating a selection of linking atoms to compose a scaffold on the metal center that will optimize reactions.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of producing a catalyst for harvesting carbon dioxide from a gas mixture, comprising the steps of:
    developing preliminary information regarding the catalyst for harvesting carbon dioxide from the gas mixture wherein said preliminary information includes potential energy surfaces around a metal center that will optimize reaction with carbon dioxide,
    said step of developing preliminary information regarding the catalyst for harvesting carbon dioxide from a gas mixture including using molecule mimics wherein said molecule mimics are 1,4,7,10-tetraacyclododedacane and 1,5,9-triazacyclododedacane,
    using said preliminary information for generating a selection of linking atoms that compose a scaffold on said metal center that will optimize reaction with carbon dioxide, and
    using said preliminary information and said selection of linking atoms that compose a scaffold on said metal center to produce the catalyst for harvesting carbon dioxide from the gas mixture.

2. The method of producing a catalyst for harvesting carbon dioxide from a gas mixture of claim 1 wherein said metal center is a zinc metal center.

3. The method of producing a catalyst for harvesting carbon dioxide from a gas mixture of claim 1 wherein said metal center is a copper metal center.

* * * * *